(12) United States Patent
Unuma et al.

(10) Patent No.: US 7,811,203 B2
(45) Date of Patent: Oct. 12, 2010

(54) WALKER BEHAVIOR DETECTION APPARATUS

(75) Inventors: Munetoshi Unuma, Hitachinaka (JP); Fumitaka Otsu, Yachiyo (JP); Hideki Inoue, Hitachi (JP); Shinobu Satou, Yokohama (JP); So Higuchi, Yokohama (JP)

(73) Assignees: Hitachi, Ltd., Tokyo (JP); Hitachi Advanced Systems Corporation, Yokohama-shi (JP)

( * ) Notice: Subject to any disclaimer, the term of this patent is extended or adjusted under 35 U.S.C. 154(b) by 0 days.

(21) Appl. No.: 11/528,329

(22) Filed: Sep. 28, 2006

(65) Prior Publication Data

US 2007/0072158 A1    Mar. 29, 2007

(30) Foreign Application Priority Data

Sep. 29, 2005    (JP)    .............................. 2005-284426

(51) Int. Cl.
A63B 71/00    (2006.01)
(52) U.S. Cl. ................................ 482/8; 482/1; 701/213
(58) Field of Classification Search .................. 482/54, 482/8, 3; 434/247; 701/213–216; 600/587
See application file for complete search history.

(56) References Cited

U.S. PATENT DOCUMENTS

| | | | | |
|---|---|---|---|---|
| 5,976,083 | A * | 11/1999 | Richardson et al. | 600/300 |
| 6,013,007 | A * | 1/2000 | Root et al. | 482/8 |
| 6,135,951 | A * | 10/2000 | Richardson et al. | 600/300 |
| 6,148,262 | A * | 11/2000 | Fry | 701/213 |
| 6,522,266 | B1 * | 2/2003 | Soehren et al. | 340/988 |
| 6,605,038 | B1 * | 8/2003 | Teller et al. | 600/300 |
| 6,837,827 | B1 * | 1/2005 | Lee et al. | 482/8 |
| 6,882,955 | B1 | 4/2005 | Ohlenbusch et al. | |
| 6,976,083 | B1 * | 12/2005 | Baskey et al. | 709/232 |

(Continued)

FOREIGN PATENT DOCUMENTS

JP    8-261755 A    10/1996

(Continued)

OTHER PUBLICATIONS

Journal of paper A by The Institute of Electronics, Information and Communication Engineers, vol. J87-A, No. 1, pp. 78-86, Jan. 2004.

(Continued)

*Primary Examiner*—Fenn C Mathew
*Assistant Examiner*—Andrew M Tecco
(74) *Attorney, Agent, or Firm*—Crowell & Moring LLP

(57) ABSTRACT

A behavior of a walker is detected according to combination of detection of the walking behavior on a level and an altitude variation of the walker to more accurately detect the behavior of the walker. A burned calorie can be obtained according to the type of the walking behavior. An altitude variation can be obtained more accurately by integrating altitude variation only at sections with vertical movement during walking. A stride is estimated according to the behavior of the walker in consideration of the vertical movement. Obtained position and traveling direction are used for compensating values in inertial navigation system. The behavior with and without vertical movement is used in a walker navigator and a worker observing system including a worker terminal carried by the walker for detecting the behavior of the worker and a worker observing terminal for providing the detected position and behavior of the walker.

14 Claims, 15 Drawing Sheets

U.S. PATENT DOCUMENTS

| | | | |
|---|---|---|---|
| 7,278,966 B2 * | 10/2007 | Hjelt et al. | 600/300 |
| 7,305,303 B2 * | 12/2007 | Soehren et al. | 701/221 |
| 2001/0048364 A1 * | 12/2001 | Kalthoff et al. | 340/573.1 |
| 2004/0046692 A1 * | 3/2004 | Robson et al. | 342/357.06 |
| 2004/0064286 A1 | 4/2004 | Levi et al. | |
| 2005/0033200 A1 * | 2/2005 | Soehren et al. | 600/595 |
| 2005/0033515 A1 * | 2/2005 | Bozzone | 701/214 |
| 2005/0068169 A1 * | 3/2005 | Copley et al. | 340/539.13 |
| 2005/0107216 A1 * | 5/2005 | Lee et al. | 482/8 |
| 2005/0137793 A1 * | 6/2005 | Krull et al. | 701/210 |
| 2005/0197237 A1 * | 9/2005 | Chen | 482/8 |
| 2005/0209061 A1 * | 9/2005 | Crawford et al. | 482/54 |
| 2005/0288154 A1 * | 12/2005 | Lee et al. | 482/3 |
| 2006/0098772 A1 * | 5/2006 | Reho et al. | 377/24.2 |
| 2007/0021269 A1 * | 1/2007 | Shum | 482/8 |
| 2007/0173378 A1 * | 7/2007 | Jamsen et al. | 482/8 |
| 2007/0243855 A1 * | 10/2007 | Hoffman et al. | 455/404.2 |

FOREIGN PATENT DOCUMENTS

| | | |
|---|---|---|
| JP | 8-285582 A | 11/1996 |
| JP | 10-113343 A | 5/1998 |
| JP | 10-148539 A | 6/1998 |
| JP | 11-325929 A | 11/1999 |
| JP | 11-347021 A | 12/1999 |
| JP | 2000-97722 A | 4/2000 |
| JP | 2001-289632 A | 10/2001 |
| JP | 2002-31536 A | 1/2002 |
| JP | 2002-48589 A | 2/2002 |
| JP | 2002-139340 A | 5/2002 |
| JP | 2002-217811 A | 8/2002 |
| JP | 2002-318122 A | 10/2002 |
| JP | 2004-85511 A | 3/2004 |
| JP | 2004-138513 A | 5/2004 |
| JP | 2005-91184 A | 4/2005 |
| JP | 2005-257644 A | 9/2005 |
| WO | WO 2005/004719 A1 | 1/2005 |

OTHER PUBLICATIONS

Partial European Search Report dated Jan. 11, 2007 (four (4) pages).
Japanese office action mailed May 11, 2010 with English translation.

* cited by examiner

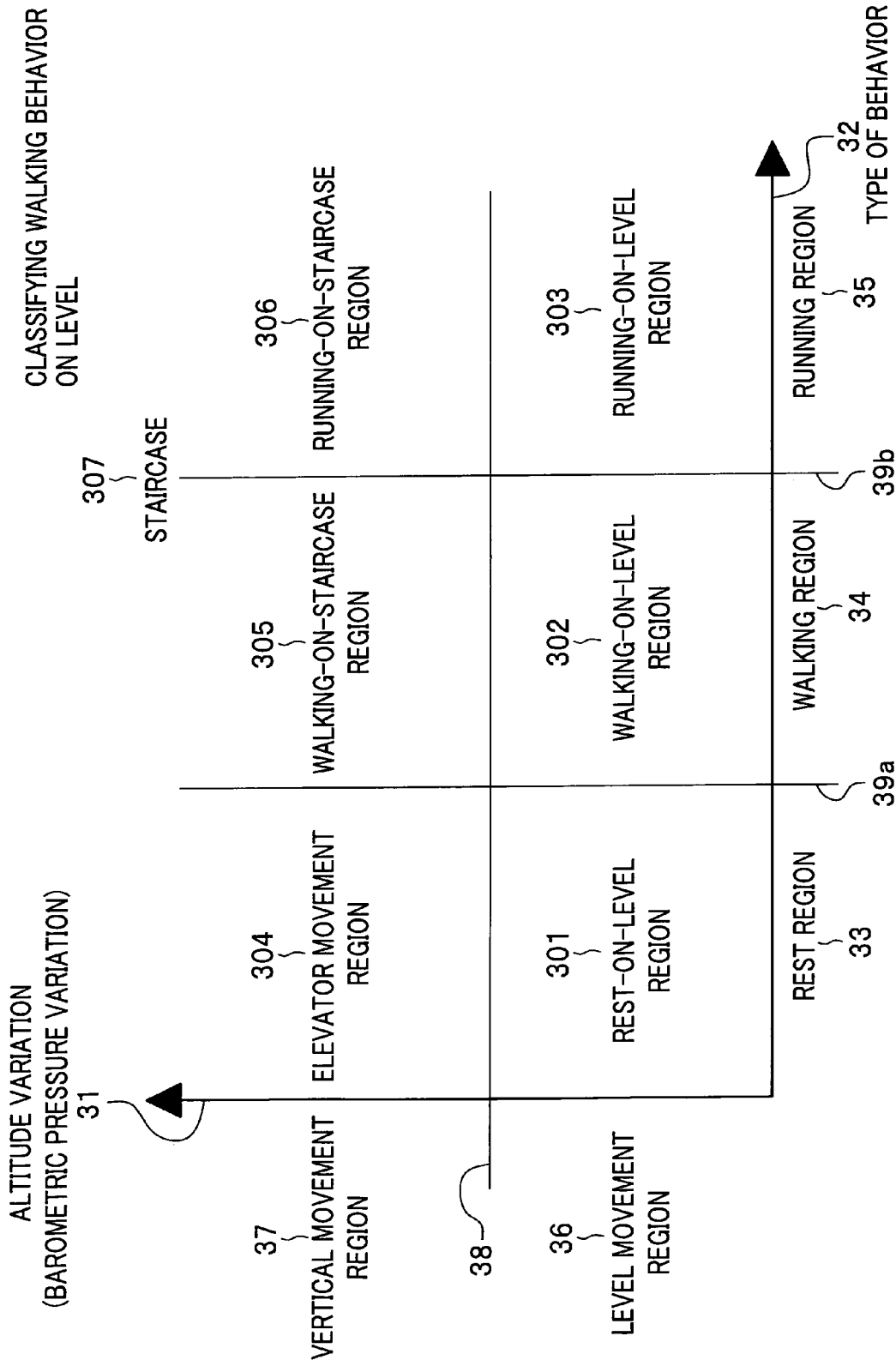

WALKER BEHAVIOR DETECTION APPARATUS

BACKGROUND OF THE INVENTION

1. Field of the Invention

The present invention relates to a walker behavior detection apparatus.

2. Description of the Related Art

A walking status is recognized by observing vertical movement accompanying walking using an acceleration sensor and spectrum-analyzing the vertical movement. For example, Japanese Laid-open Patent Application Publication No. 10-113343 discloses such a technology. Further, a position of a walker is estimated in accordance with the recognized walking status by comparing the detected walking status with geographic data of, for example, passages in a building or roads outside the building.

Further, a moving distance is calculated by estimating stride from the recognized walking status. For example, Japanese Laid-open Patent Application Publication No. 2004-085511 and Journal of paper A by the Institute of Electronics, Information and Communication Engineers, Vol. J87-A, No. 1, pp 78-86, January 2004 disclose such a technology.

In the documents, the walking status is recognized by observing physical forces (an acceleration, an angular velocity, and like) generated by a movement of a walker. Walking on a staircase can be recognized only by the acceleration and the angular velocity from a waveform observed during the walking on the staircase. However, walking on the staircase may be erroneously recognized as walking on a level which resembles walking on the staircase. Further, if a positional compensation is made by comparing the motion recognition with geographic information, the erroneous recognition may cause judgment that the position is at an incorrect place. Further, the prior art position determination method does not consider a walking direction of the walker.

In the prior art, the moving distance is calculated by estimating a stride. However, it does not consider moving distances during climbing and descending the staircase.

SUMMARY OF THE INVENTION

A first aspect of the present invention provides a walker behavior detection apparatus comprising: detecting means for detecting a horizontal walking behavior of a walker regarding a level; altitude variation detecting means for detecting altitude variation of the walker; and estimating means for estimating a walking behavior of the walker on the basis of a combination of the horizontal walking behavior and the detected altitude variation.

A second aspect of the present invention provides a walker behavior detection apparatus comprising: walker behavior detecting means for detecting a behavior of a walker; a storage for storing geographical information corresponding to the detected behavior of the walker; and searching means for searching a part of the geographical information corresponding to the detected behavior of the walker to detect position information and traveling direction information on the basis of the searched part.

BRIEF DESCRIPTION OF THE DRAWINGS

The object and features of the present invention will become more readily apparent from the following detailed description taken in conjunction with the accompanying drawings in which:

FIG. 3 is a classifying table according to the first embodiment;

The same or corresponding elements or parts are designated with like references throughout the drawings.

DETAILED DESCRIPTION OF THE INVENTION

The present invention provides a walker behavior detection apparatus capable of accurately recognizing a walking status though the walker is in a walking status with vertical movement.

In the present invention, a behavior of a walker is recognized using a combination of recognizing a walking behavior on a level and simultaneously detecting vertical movement to improve a recognition accuracy.

First Embodiment

Figure 1:
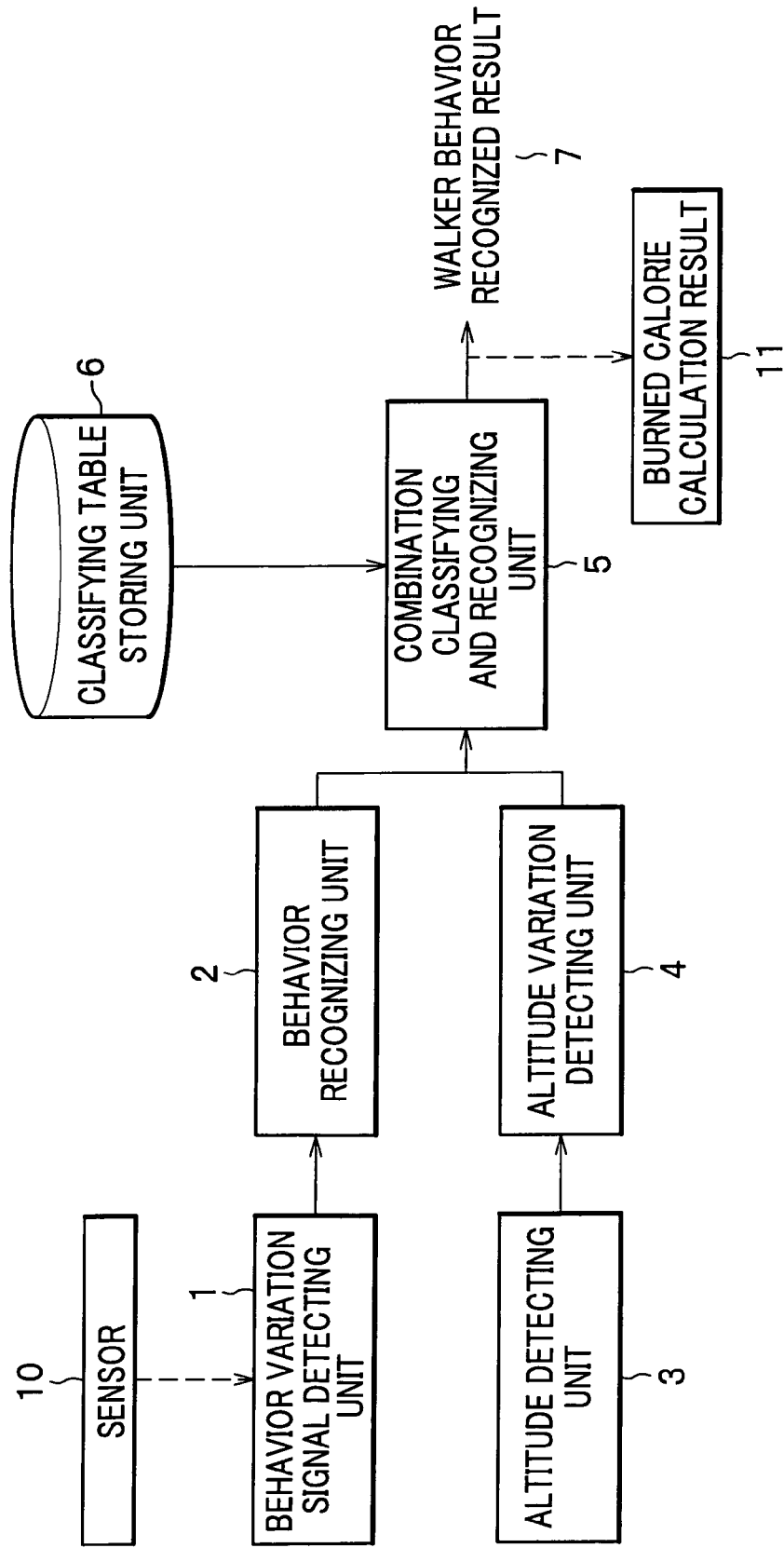
FIG. 1 is a block diagram of a walker behavior detection apparatus according to a first embodiment of the present invention.

FIG. 1 is a block diagram of a walker behavior detection apparatus according to a first embodiment of the present invention. A behavior variation signal detecting unit 1 detects a behavior variation signal. The behavior variation signal is a signal generated by a sensor 10 for detecting an acceleration variation accompanying a movement of the walker, or a signal of an angular velocity, a displacement of a joint of the walker, a variation in an intensity of an electric field transmitted by a base station according to a position or the movement of the walker, a gyration variation of the walker, or the like. A behavior recognizing unit 2 recognizes a behavior or a variation of the behavior such as "walking" and "running" of the walker. As the behavior variation signal detecting unit 1, for example, an acceleration sensor (for example, see FIGS. 14 to 16) is available for detecting upward and downward acceleration variation accompanying the behavior of the walker, and the behavior recognizing unit 2 recognizes the behavior variation of the walker such as "walking" and "running" from an amount of characteristic derived by frequency-analyzing the behavior variation signal. Further, as the behavior variation detection unit 1, a receiver, carried by the walker, for receiving a radio wave transmitted from the base station is also available. The behavior recognizing unit 2 may recognize the behavior and/or the variation in the behavior of the walker using an amount of characteristic of a variation in a waveform of an electric field intensity of a radio wave observed while the walker moves. An altitude detecting unit 3 detects an altitude of the walker. As the altitude detecting unit 3, for example, a barometric pressure sensor (for example, see FIG. 15) for observing a variation in the barometric pressure is available. In addition, the altitude detecting unit 3 may detect an altitude using altitude information obtained by a satellite positioning unit such as a GPS (Global Positioning System) unit (for example, see FIG. 14) or an altitude by referring to a table indicating correspondence between ID information of an RFID or a wireless beacon and the previously measured altitude information. An altitude variation detecting unit 4 detects a variation in the altitude of the walker, i.e., a variation in the altitude per unit time interval. For example, an altitude variation is detected by differentiating a barometric pressure data observed with the barometric pressure sensor per unit time interval. A combination classifying and recognizing unit 5 classifies the results from the behavior recognizing unit 2 and the altitude variation detecting unit 4 with a classifying table stored in a classifying table storing unit 6 to output a walker behavior recognition result 7 of the walker.

Figure 2:
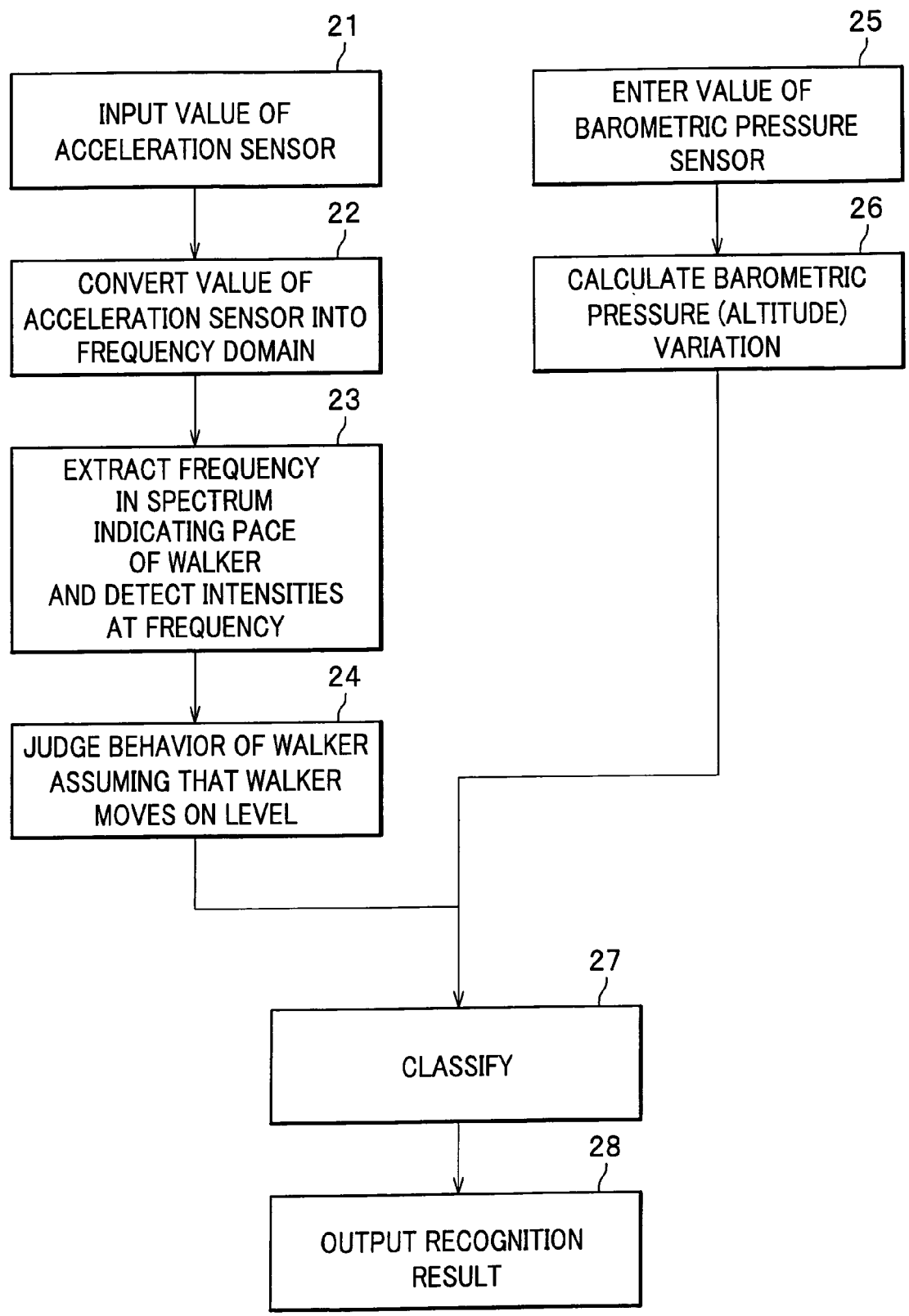
FIG. 2 shows a flowchart of the walker behavior detection apparatus according to the first embodiment.

With reference to FIG. 2, will be described a flow of a process in the walker behavior detection apparatus. Regarding FIG. 1, various types of units are available for the behavior variation signal detecting unit 1 and the altitude detecting unit 3. However, to simplify the description, will be described an example in which the acceleration is detected as the behavior detection signal, and the barometric pressure sensor is used as the altitude detecting unit 3.

A value of the acceleration sensor is inputted in a step 21. For example, an analog signal outputted by the acceleration sensor is read with an A/D converter. The read value of the acceleration sensor is converted into a frequency domain with an FFT (fast Fourier transform) or the like in a step 22. In a step 23, a frequency in a spectrum indicating a pace of the walker (pace spectrum) is extracted from data obtained by converting the output of the acceleration sensor into the frequency domain and intensities are detected. In a step 24, the intensity of the spectrum at the frequency is classified with a membership function to recognize the behavior of the walker such as "walking" and "running" with the membership function (similar to the recognizing unit disclosed in Japanese Laid-open Patent Application Publication No. 10-113343). Thus, the behavior of the walker is recognized with an assumption that the walker moves on a level.

In a step 25, a value of the barometric pressure sensor is read with an A/D converter at the same time as in the acceleration sensor. The entered value of the barometric pressure sensor is calculated by differentiating at a unit time interval in the step 26 to convert it into a variation in the barometric pressure (barometric pressure variation).

In a classifying process in a step 27, a walking behavior is recognized by combining two types of judging results from the recognizing result in the step 24 of the walking behavior and the calculation result of the barometric pressure variation in the step 26. In the step 27, the following process is executed.

In the following descriptions, there is exemplified a case in which a staircase or an elevator is used for the walker to move vertically. Further an example of a content of the classifying table 6 in FIG. 1 is made as shown in FIG. 3.

When the walker moves on a level (flat place), in which case there is no barometric pressure variation, the barometric pressure variation becomes that linked to a sea level pressure at that moment. Although the barometric pressure may rapidly vary because a depression or a typhoon passes, the variation is equal to or less than several hPa. For example, a maximum barometric pressure variation at Yokohama when typhoon No. 11 of 2005 passes was 5.1 hPa for one hour from 3:00 a.m. to 4:00 a.m. on (August) 26. When the barometric variation is converted into an altitude variation, the value is about 43 m per hour. Thus the barometric variation is considered to be an altitude variation of about 70 cm per minute. As compared with this, when the walker climbs a staircase, the walker generally moves across about 4 m of one floor in about 10 to 15 seconds. Thus, the walker moves about 16 m for one minute. The barometric variation by the movement of the walker is about twenty times that by the approaching typhoon. Accordingly, the movement can be judged as vertical movement using the barometric variation with a threshold. When the barometric variation is smaller than the threshold, the movement can be judged as a movement on the level. In FIG. 3, the abscissa 32 represents types of walking behavior and the ordinate 31 represents an altitude variation (barometric pressure variation). A numeral 38 represents the threshold for judgment between presence and absence of the vertical movement in the barometric variation. Thus, a level movement region 36 under the threshold 38 with a small barometric variation represents the absence of the vertical movement as a level movement. Similarly, a vertical movement region 37 above the threshold 38 with a large barometric variation represents the presence of the vertical movement.

However, only the barometric pressure variation cannot provide judgment of the walking behavior of the walker. Then, the walking behavior of the walker is judged by a combination of the judgment based on the barometric pressure and the judgment made in the step 24. Thus, the judgment in the step 24 is made regarding the abscissa 32 in FIG. 3.

In FIG. 3, references 39*a* and 39*b* represent thresholds for types of the behavior of the walker. On the left side of the threshold 39*a* is a rest region 33. On the right side of the threshold 39*b* is a running region 35. Between the thresholds 39*a* and 39*b* is a walking region 34.

When the barometric pressure variation is judged as the level movement (level movement region 36) and the type of behavior is judged as a rest in the step 24, the behavior of the walker is judged as a rest on the level (classified into a rest-on-level region 301), at an overlapped region between the level movement and a status of rest on the level. Similarly, when the barometric pressure variation is judged as the level movement (classified into a level movement region 36) and the type of the behavior is judged as walking (classified into the walking region 34), the walking behavior of the walker is judged as walking on the level (classified into a walking-on-level region 302).

Similarly, when the barometric pressure variation is judged as the level movement (the level movement region 36) and the type of the behavior is judged as walking (the walking region 34), the walking behavior of the walker is judged as walking on the level (a walking-on-level region 302). When the type of the behavior is judged as running (the running region 35), the walking behavior of the walker is judged as running on the level (a running-on-level region 303).

When the barometric pressure variation is judged as the presence of vertical movement (the vertical movement region 37) and the type of the behavior is judged as a rest in the step 24, the walking behavior of the walker is judged as movement on an elevator (elevator movement region 304).

Similarly, when the barometric pressure variation is judged as the presence of the vertical movement (vertical movement region 37) and the type of the behavior is judged as walking (walking region 34), the behavior of the walker is judged as walking on a staircase (walking-on-staircase region 305). When the barometric pressure variation is judged as the presence of the vertical movement and the behavior of the walker is judged as running, the behavior of the walker is judged as running on the staircase (running-on-staircase region 306). The recognition result is outputted in the step 28.

Figure 4A:
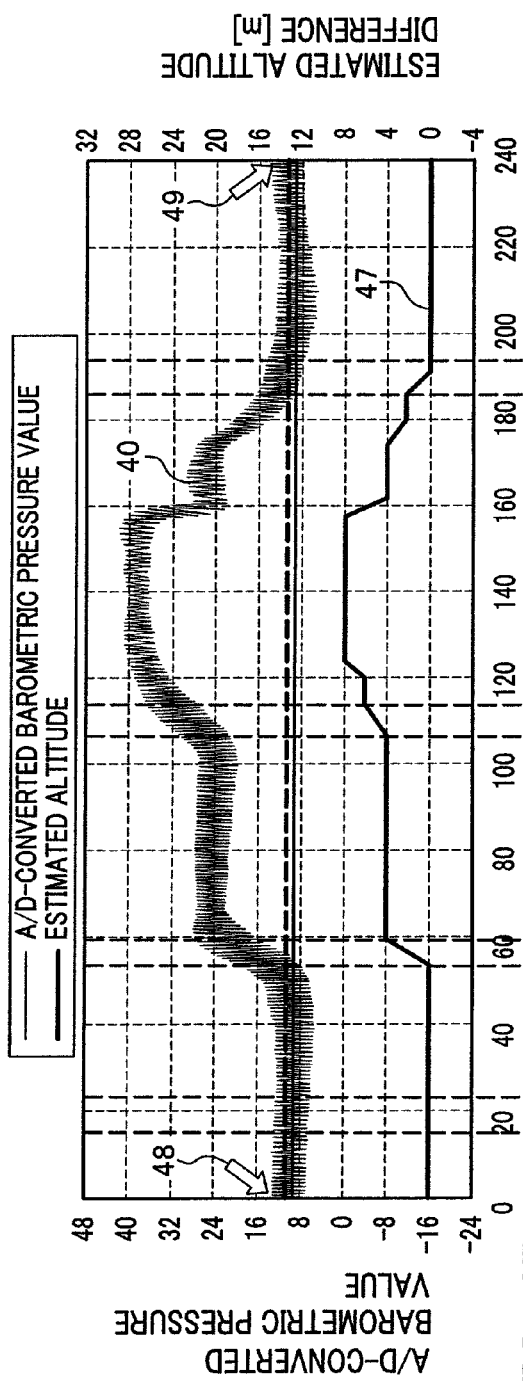
FIG. 4A is a graphical drawing for showing an example of altitude estimation according to the first embodiment.
Figure 4B:
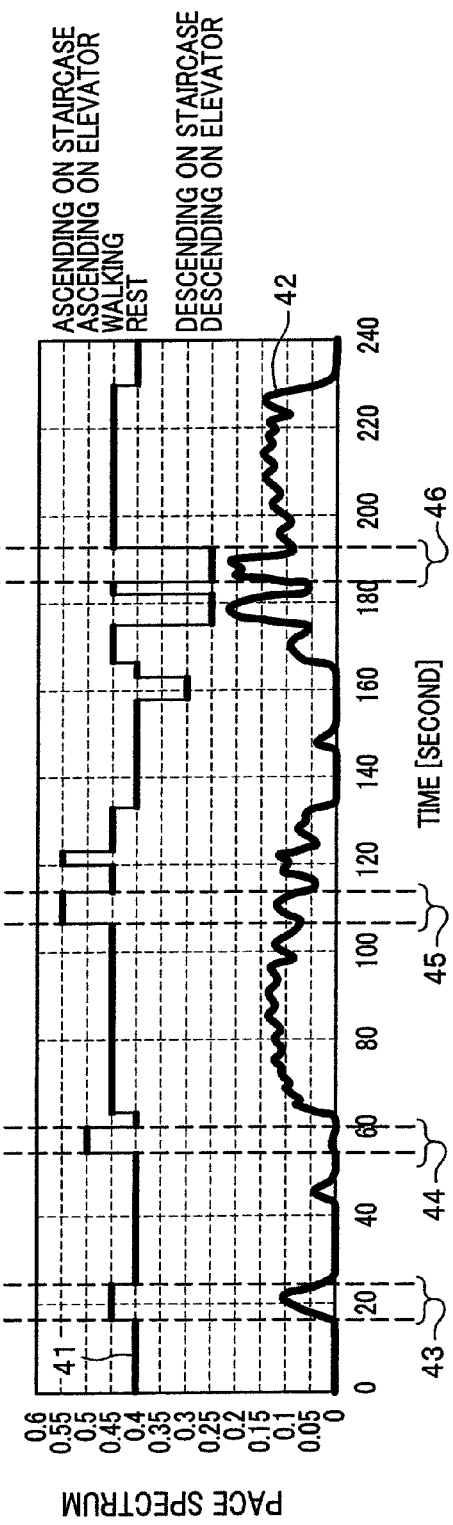
FIG. 4B is a graphical drawing for showing an example of behavior judgment regarding the result in FIG. 4A.

FIGS. 4A and 4B show an example of judgment. Abscissas represent time. A waveform 40 represents barometric pressure data and the ordinate on the left side in FIG. 4A represents AD-converted values and the ordinate on the right side in FIG. 4A represents altitudes after conversion.

The output of the barometric pressure sensor is A/D-converted after conversion of the output such that a conversion output increases in value as the pressure decreases as the altitude increases and decreases as the pressure increases as the altitude decreases.

A waveform 42 indicates intensities of pace spectrum extracted in the step 23. The ordinate on the left side in FIG. 4B represents spectrum intensities. When a spectrum intensity exceeds 0.05, the behavior is judged as the walking status, and when the spectrum intensity exceeds 0.4, the behavior is judged as the running status. In this example, because there is no spectrum intensity exceeding 0.4, the walker only rests and/or walks in this measuring interval. A waveform 41 represents a judging result read on an ordinate on the right of FIG. 4B. The behavior of the walker between 0 and 20 seconds is judged as a rest status. At a section 43, there is substantially no barometric pressure variation because the intensity 42 of the pace spectrum is approximately from 0.05 to 0.1 (the walking status). Then, there is no barometric pressure variation with the walking status and thus judged as walking on the level. At a section 44, there is a barometric variation and the status is a rest. Thus, the behavior is judged as movement by an elevator.

In this event, using a sign of barometric pressure variations, it can be judged that the behavior of the walker is judged as an upward movement by the elevator because the sign is positive at the section 44. At the section 45, the barometric pressure variation has a positive variation and thus, indicates the walking status from the pace spectrum. Thus, the walker is judged to climb the staircase. At a section 46, the barometric pressure variation is negative and the status of the walker is judged as walking, so that the walker is judged to be descent on a staircase.

As mentioned above, the walking status accompanied by the vertical movement can be recognized by combining the recognition in the behavior recognizing unit 2 and the recognition on the basis of barometric pressure variation in the altitude variation detecting unit 4.

Figure 5:
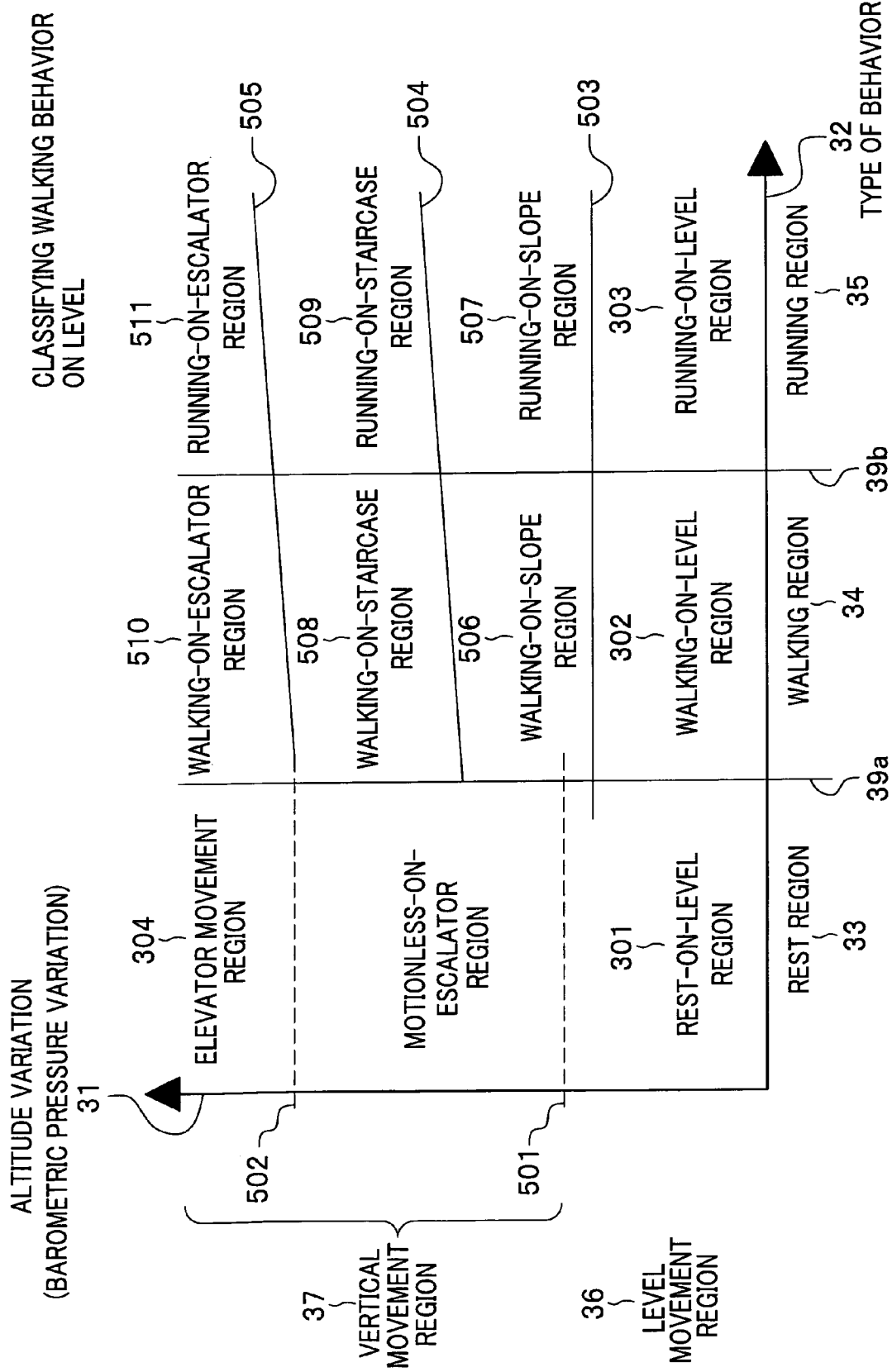
FIG. 5 is a classifying table according to the first embodiment in which the number of recognition classes is increased.

FIG. 5 shows a modification in which the thresholds for the altitude variation are more than those in FIG. 3 and threshold functions are inclined in accordance with severity of the walking action (the running is severer than the walking) to discriminate more behaviors of the walker. A slope and an escalator are added to the staircase as the vertical movement to be recognized. There are threshold values 501 and 502 of the barometric pressure variation in a rest of the walker. The threshold value 501 is for recognizing the walker in a rest on an escalator, and the threshold value 502 is for recognizing the walker in a rest on the elevator. Between the thresholds 501 and 502 the behavior is classified into a moving on an escalator without walking (motionless-on-escalator region). The threshold values 501 and 502 are determined by ascending speeds of the escalator and the elevator, respectively. If the movement is accompanies a walking action, in which case altitude ascending variation by the walking should be additionally considered, a threshold of the barometric pressure variation should be determined in consideration of severity of walking in addition to the ascending variation by the escalator. In FIG. 5 threshold lines 504 and 505 for the barometric pressure have values becoming large as the behavior of the walker becomes running. Discrimination of the behavior of the walker is made from a relation between the result recognized in the step 24 and the threshold of the barometric pressure as shown in FIG. 5. The recognizing result is outputted by the step 28.

Further, walking on a slope and running on the slope is discriminated from walking on the level and running on the level with a threshold 503.

Thus, the behavior of the walker is further classified into a walking-on-slope region 506, a running-on-slope region 507, a walking-on-staircase region 508, a running-on-staircase region 509, a walking-on-escalator region 510, and a running-on-escalator region 511.

As described in the embodiment, a plurality of threshold values for the barometric pressure are provided in accordance with vertical moving methods to increase the number of the recognized types of the walking behavior accompanied by the vertical movement.

The above-mentioned embodiment is limited to the recognition of the walking behavior. However, a burned calorie can be calculated from the walking behavior. For example, the burned calorie varies in accordance with a difference in a type of walking behavior such as walking on the level, and walking on the staircase. Thus, a table of burned calories, corresponding to walking behaviors, is previously prepared, and the burned calorie associated with the walking behavior can be calculated with reference to Table (1).

Table (1) shows an example of relation between types of the walking behavior and the burned calories.

TABLE 1

| TYPE | REST | WALKING ON LEVEL | WALKING ON SLOPE | WALKING ON STAIRCASE |
|---|---|---|---|---|
| KCAL/MIN | C1 | C2 | C3 | C4 |

In FIG. 1, for this operation a burned calorie calculating unit 11 is add which calculates the burned calorie in accordance with the walking behavior recognized result 7.

As mentioned above, according to the embodiment, the burned calorie can be detected in accordance with the walking behavior. In addition, a total burned calorie can be calculated by integration in accordance with the detected type of the walking behavior.

Figure 9:
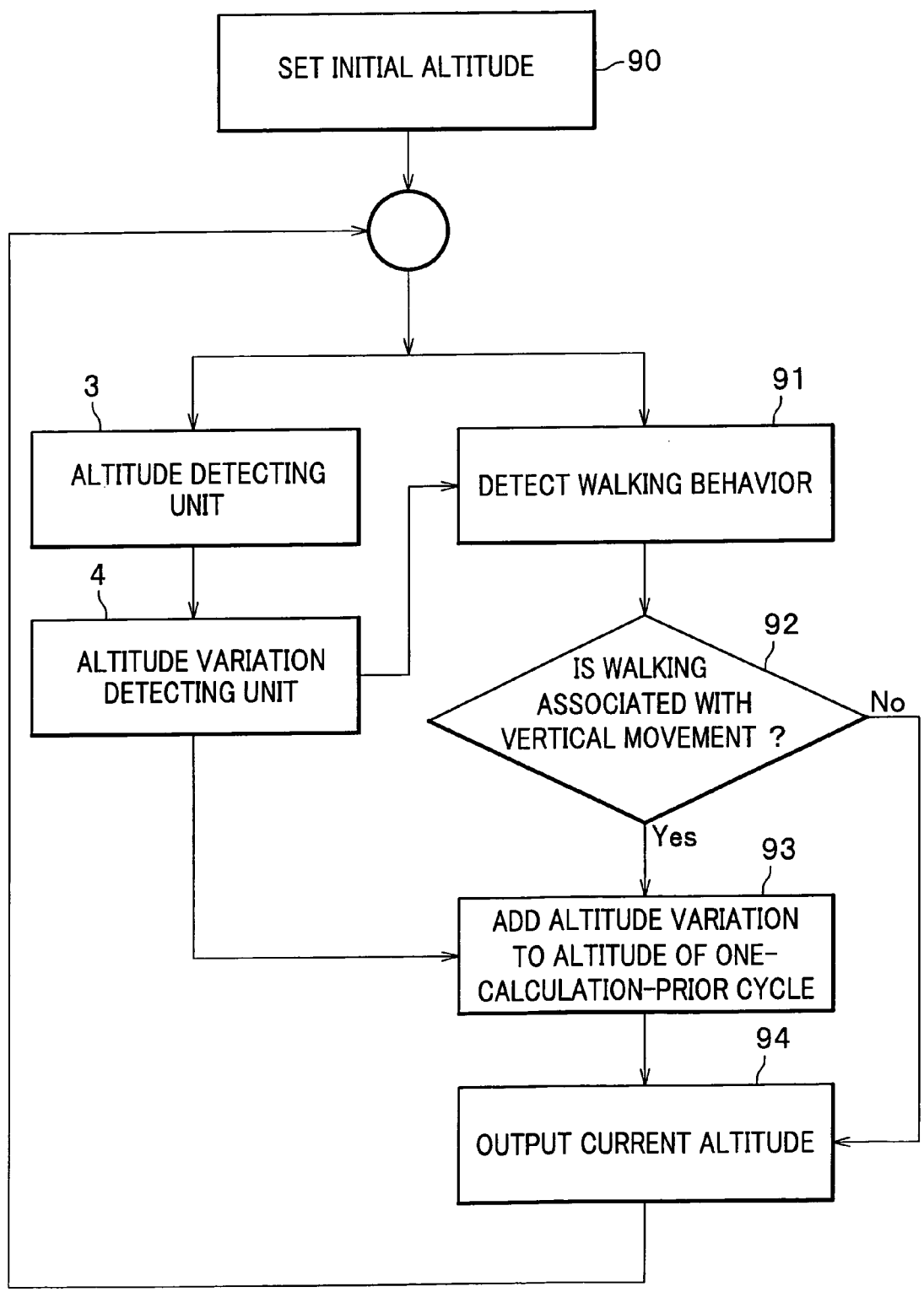
FIG. 9 shows a flowchart of altitude compensation using the walker behavior detection apparatus according to a modification in the first embodiment.

With reference to FIG. 9 will be described a modification in which the altitude detected by the barometric pressure sensor is compensated with the walking behavior recognized result 7. The waveform 40 in FIG. 4 represents the output of the altitude detecting unit (a barometric pressure sensor) 3. The data is obtained in an example in which an observation is made at the same position (the same altitude) at start time (time=0 second) and end time (time=240 second). Accordingly, the altitudes at the start time and the end time should be the same. However, the altitude at the end time slightly increases from the altitude at the start time. This is because, as previously described in the example describing the typhoon, the barometric pressure varies by approach of a depression and the like as time passes. In the presence of such the barometric variation the altitude obtained by the barometric pressure measured by a barometer may include an error in the altitude obtained by the barometric pressure sensor. Then, with a processing flowchart shown in FIG. 9, the error is compensated. First, an initial altitude is set in a step 90. This can be made by the user through a manual setting or with altitude information from a GPS unit. Next, the walking behavior is detected in a step 91 (for example, the process shown in FIG. 2). It is judged, in a step 92, whether the walking is associated with the vertical movement. If the walking behavior is associated with the vertical movement, because the altitude variation detected in the step 4 is caused by a barometric pressure accompanied by the vertical movement, a process is made in which the altitude variation is added to the altitude of one-calculation-prior cycle to output the resultant altitude in a step 93. If the walking behavior judged to be without the vertical movement, because the value of the barometric variation currently observed is not the altitude variation accompanied by the vertical movement, without the process in a step 93, the value of the altitude of one-calculation-prior cycle is outputted as the current altitude in step 94. Hereinafter, the same process is repeated to detect the altitude. A waveform 47 in FIG. 4 shows a result of the process in which the altitude difference between the arrows 48 and 49 is compensated with a correct altitude. In this modification, the barometric pressure variation (sea-level pressure) during the vertical movement is not considered. This is because time duration during the vertical movement is shorter than that during walking on the level, so that this does not result in a large error if no consideration of the sea-level pressure variation during the vertical movement is made.

According to this modification, the barometric pressure variation is considered only at sections in which the walking behavior is associated with the vertical movement to exclude the influence of the sea-level pressure variation.

Second Embodiment

Figure 6:
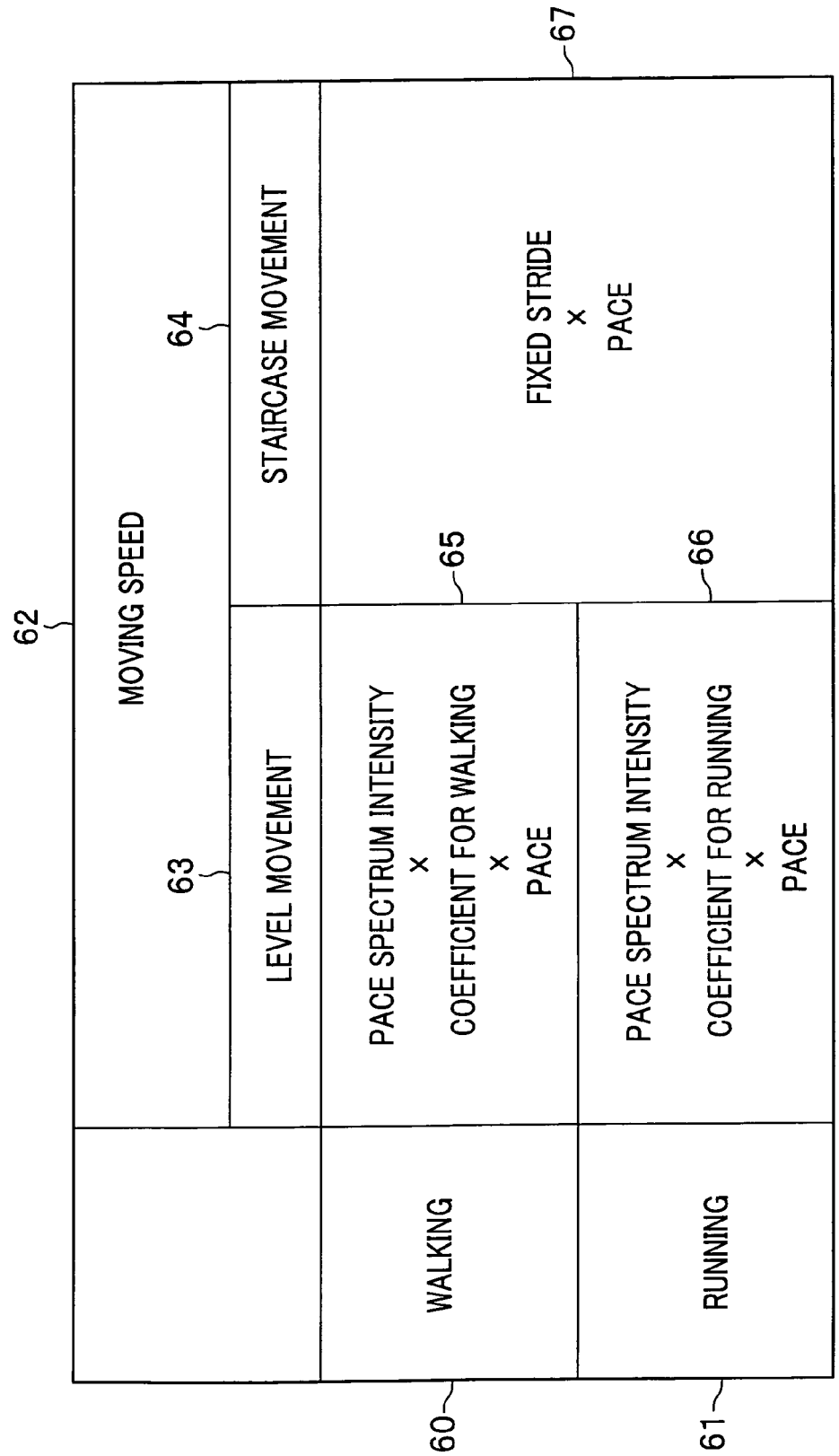
FIG. 6 is a table for stride estimation according to a second embodiment.
Figure 7:
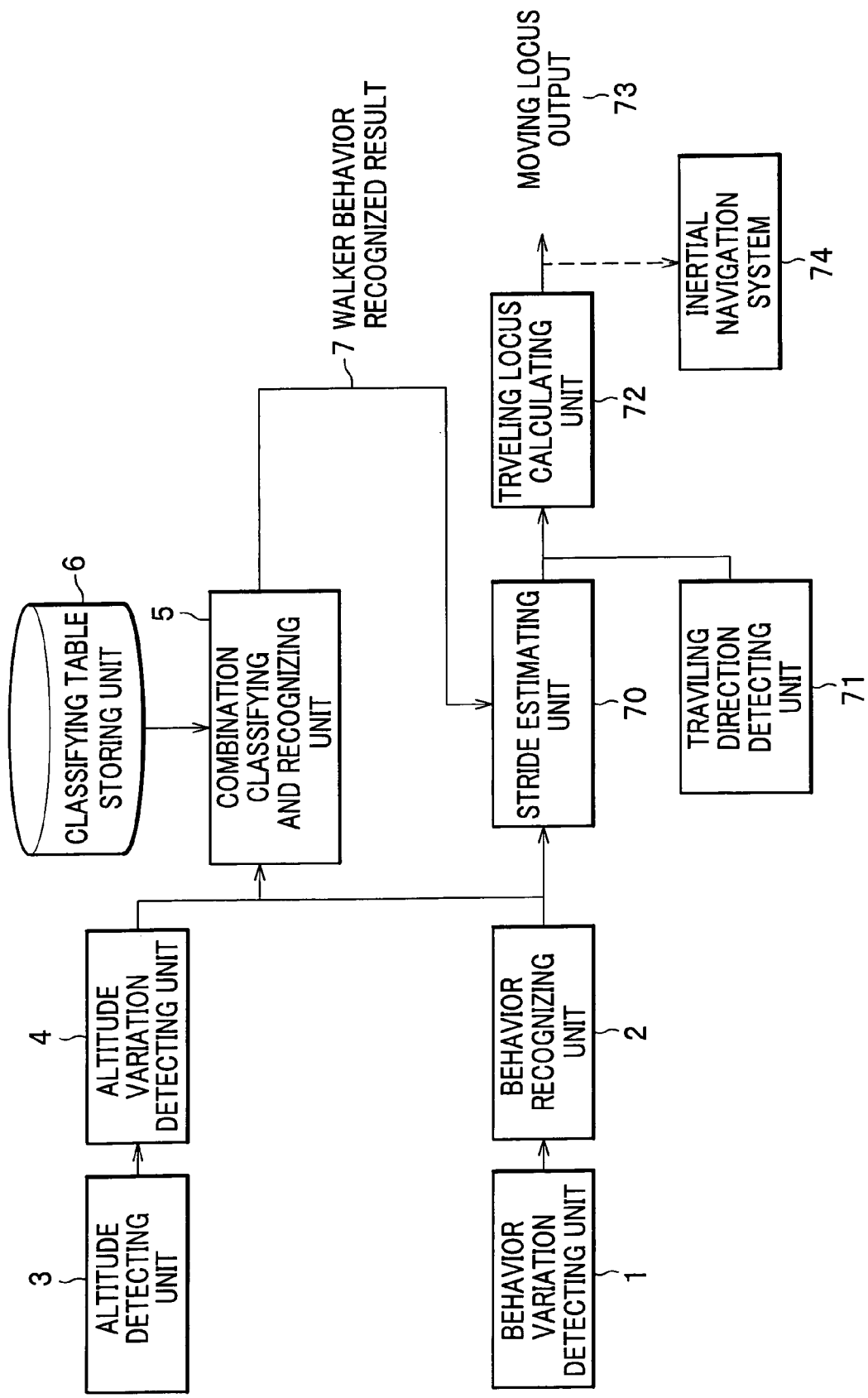
FIG. 7 is a block diagram of the behavior detection apparatus for estimating the stride and detecting a position according to the second embodiment of the present invention.

With reference to FIGS. 6 and 7 will be described a position detection apparatus, using the walking behavior detection in the first embodiment, capable of estimating an accurate stride in walking even with vertical movement using the recognized walking behavior as mentioned above to apply it to a position detection technology according to a second embodiment of the present invention. FIG. 7 is a block diagram of the behavior detection apparatus for estimating the stride and detecting a position. FIG. 6 is a table for estimating the stride. The estimation of a traveling speed (moving distance) of the walker on the level is disclosed in Japanese laid-open patent application publication No 2004-085511 and Journal of paper A by the Institute of Electronics, Information and Communication Engineers, Vol. J87-A, No. 1, pp 78-86, January 2004. In the embodiment, a traveling speed (moving speed) of the walker on the level is estimated as follows:

(1) An acceleration variation waveform in the vertical direction is frequency-analyzed in order to extract a frequency indicating the pace and detect the spectrum intensity.

(2) The stride is

Stride=Pace Spectrum Intensity×Coefficient for Each Walking Behavior

This uses the fact that, because the coefficient for each walking behavior is different between walking and running, coefficients for conversion into the strides are different from one another.

(3) The traveling speed is

Traveling Speed=Stride×Pace (4) The traveling distance is

Traveling Distance=Time-Integration of Traveling Speed

If the walker moves on the level, this estimation is made in consideration of variation in the stride caused by difference in the walking behavior, so that an accurate traveling speed can be obtained though the walker walks or runs. On the other hand, if the walker moves on the staircase, the spectrum intensity becomes different between ascending and descending (sections 45 and 46 in FIG. 4) with a result that the traveling distance becomes different between the ascending and the descending. This is because an acceleration at touching to a step during descending is greater than that during ascending. Here, sizes of steps of the staircases are substantially the same, so that the stride does not change in accordance with the walking behavior (except skipping).

Then, the stride is estimated with a stride estimating unit 70 shown in FIG. 7 designed in consideration of the vertical movement. The stride estimation unit 70 is supplied with a frequency and the spectrum intensity of the pace spectrum obtained by the behavior recognizing unit 2 and a behavior recognition result 7 as input data. With reference to FIG. 6 will be described a process in the stride estimation unit 70. The table shows various types of stride estimation. Estimation for the level movement 63 and the staircase movement 64 is made in accordance with the moving speed 62. The level movement 63 is divided into the walking 60 and the running 61 detected by a single acceleration sensor. When the behavior is recognized as a level movement 63 in the behavior recognition result output 7, stride estimation calculations 65 and 66 for the level movement are made. When the behavior is recognized as the staircase movement 64, the moving speed is obtained by a calculation 67 of a fixed stride×a pace, independently of the behavior of walking. A value of the fixed stride may be assumed to be about 30 cm which is a size of a standard step. Further, to increase an accuracy, sizes of the steps of the staircases are recorded in geographical information, and used for the size of the step where the walker passes (will be mentioned later a unit for judging which one of staircases the walker passes). After the stride (moving speed) is estimated as mentioned above, the traveling direction of the walker is detected by the traveling direction detecting unit 71. Next, a traveling locus calculating unit 72 obtains a moving locus by integration of the traveling speed and the traveling direction to provide a moving locus output 73.

Thus, according to the second embodiment, an accurate stride estimation is provided though the walking behavior is associated with the vertical movement caused by the staircase or the like, so that the moving locus can be estimated from the stride.

Further, the stride estimation may be made as follows:

When the walker behavior is recognized as walking on the level, the stride of walking on the level is estimated, and when the walker behavior is recognized as walking accompanied by the vertical movement, the stride detected on the level is compensated on the basis of the walker behavior recognized result 7 (vertical movement) to obtain a moving speed and a traveling distance of the walker.

Third Embodiment

Figure 8:
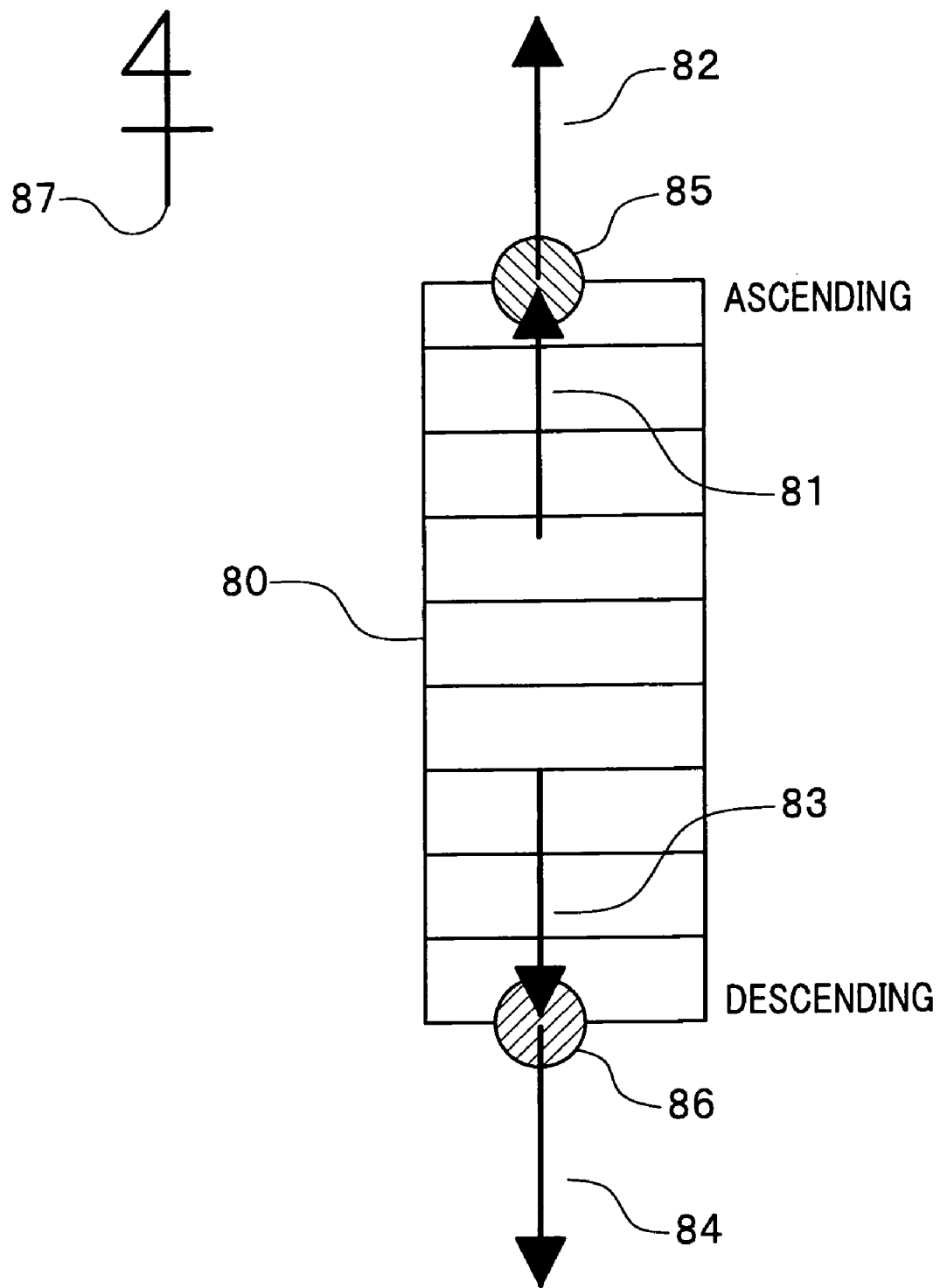
FIG. 8 is an illustration for operation during the movement on a staircase referred in the second embodiment and a third embodiment.
Figure 10:
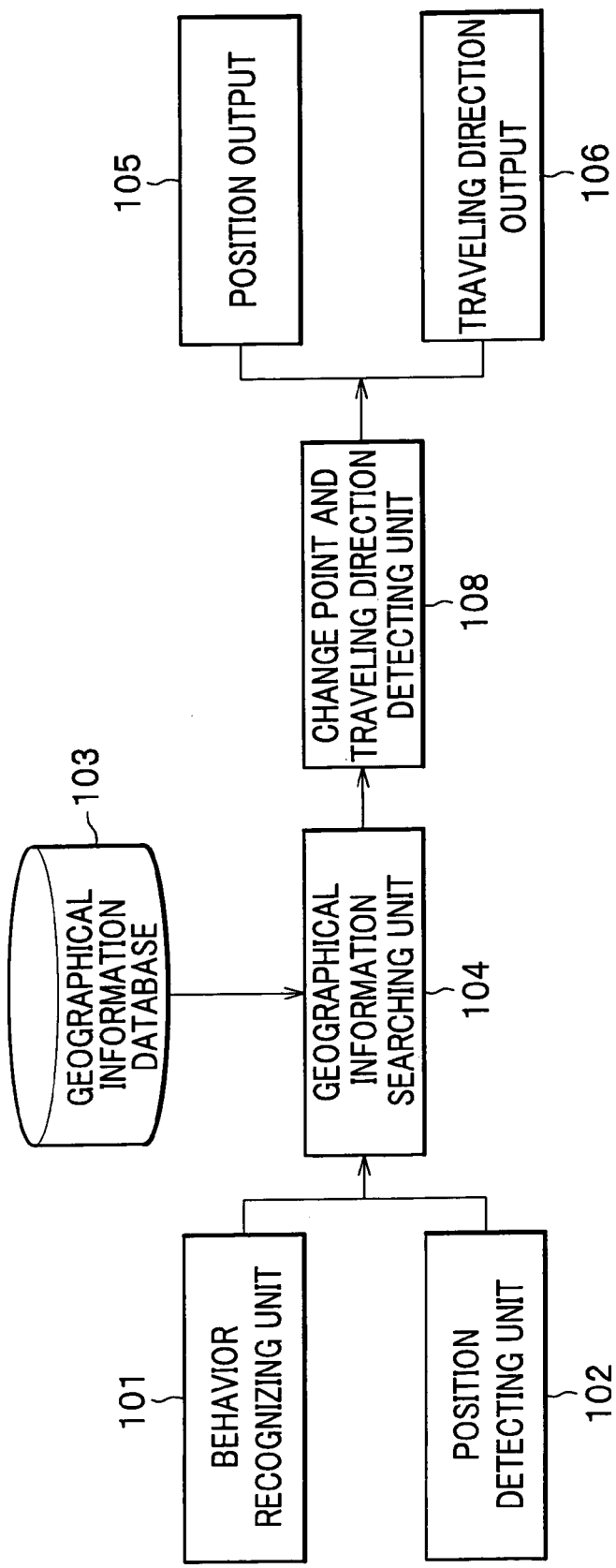
FIG. 10 is a block diagram of the behavior detection apparatus according to the third embodiment of the present invention.

With reference to FIGS. 8 and 10 will be described a position detection apparatus according to a third embodiment in which the recognized walking behavior is compared with geographical information therearound, and the position of the walker corresponding to the recognized walking behavior is estimated. FIG. 8 is an illustration for operation during the movement on the staircase. FIG. 10 is a block diagram of the third embodiment. Numeral 101 in FIG. 10 is a behavior recognizing unit, which is the same as that shown in FIG. 1, for recognizing the walking behavior with the vertical movement. Numeral 102 denotes a position detecting unit of the walker. For example, this may be the moving locus calculating unit 72 described with reference to FIG. 7, a position detecting unit using a GPS unit, or a wireless LAN. The position detection apparatus described in the third embodiment is provided to detect the position of the walker having a higher accuracy than the position information detected by the position detecting unit 102. Numeral 103 denotes a geographical information database for storing geographical information such as a position of a building, information of an internal structure and a position of a staircase, an elevator and the like, and information of outside roads and geographical information. Numeral 104 denotes a geographical information searching unit using the walking behavior. The geographical information searching unit 104 searches the geographical database 103 for a position on the geographical information corresponding to the walking behavior detected by the behavior recognizing unit 102 with rough position information detected by the position detecting unit 101. Here, the geographical information corresponding to the walking behavior means that "staircase geographical information" is for staircase walking; "elevator geographical information for an elevator movement" is for elevator movement; "escalator geographical information" is for an escalator movement; and the like. Thus, when the staircase walking is recognized, the walker is estimated to be at a place on a staircase, and the position information of the staircase can be obtained with reference to the geographical information of staircases. Assuming that there are a plurality of staircases, the geographical information searching unit 104 searches the geographical information database 103 for the geographical information corresponding to the nearest staircase on the basis of the rough position information of the walker detected by the position detecting unit 102. This provides the corresponding geographical information from a result of the behavior recognizing unit 101 and the rough current position, so that the position can be estimated from the position information in the geographical information (the above-mentioned process is the same as that disclosed Japanese Laid-open Patent Application Publication 10-113343). Further, a change point and traveling direction detecting unit 108 performs a process of a change point in the geographical information and a traveling direction using a change in the behavior of the walker to improve the detection accuracy and detect the traveling direction. With reference to FIGS. 8 and 10 will be described the process.

Numeral 80 denotes a staircase. It is assumed that the geographical information searching unit 104 judges that the walker is on the staircase 80. As shown by an arrow 87, the staircase 80 is so arranged that an ascending direction is north, and a descending direction is south. In a case that the walker moves from a section (staircase) to a section 82 (level), the result of behavior recognition of the walker is "ascending on the staircase" at the section 81, and "level walking" at the section 82. Thus, a point 85 where the recognition result of the behavior changes to "level walking" is an end of the ascending the staircase 80. Since a shape and position data of the staircase 80 are stored in the geographic information database 103, the point 85 is obtained on the basis of the information. Thus the change point and traveling direction detecting unit 108 generates a position output 105 and a traveling direction output 106. As mentioned above, referring the change point of the walking behavior provides the position information having a higher accuracy than the result searched by the geographic information searching unit 104. Further, because the ascending direction of the staircase 80 is north, the walker walks northward. Thus, the traveling direction of the walker can be detected. This is applicable to a case of descending the staircase 80. The change point and traveling direction detecting unit 108 recognizes a section 83 as "descending the staircase", and a section 84 as "level walking", and thus, the change point 86 is judged to be an end of the staircase 80 in descending. The traveling direction is judged to be the south because the walker descends the staircase 80.

As mentioned above, according to the third embodiment, the place at the walker can be estimated by comparing the recognition result of the walking behavior with the geographical information, so that the current position and the traveling direction of the walker can be detected.

Fourth Embodiment

Figure 11:
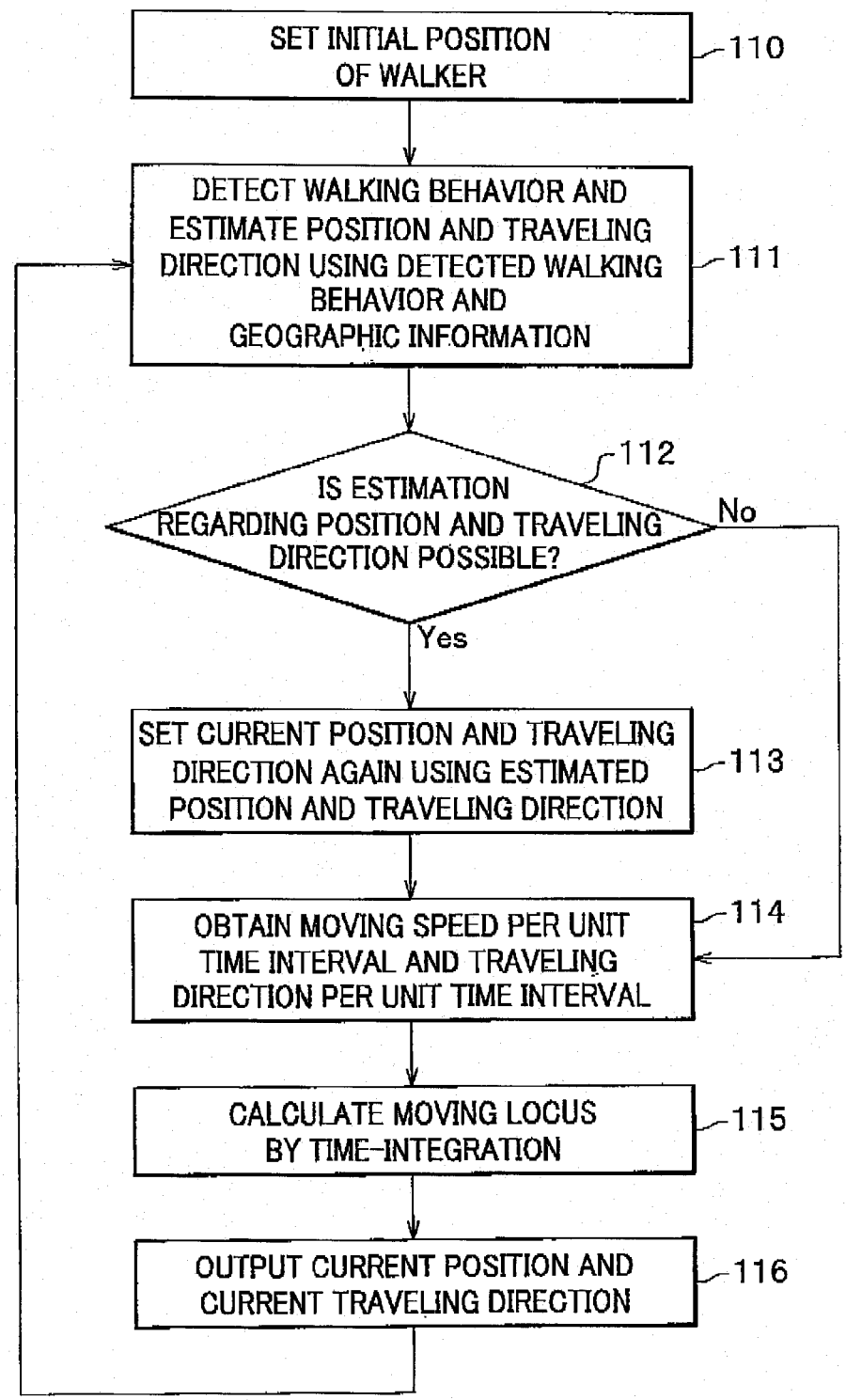
FIG. 11 shows a flowchart of position and traveling direction detection using the walker behavior detection apparatus, according to a fourth embodiment.

Next, with reference to FIGS. 11, 12, and 13 will be described a fourth embodiment in which position compensation is used in a position detection apparatus (an autonomous position detection apparatus or an inertial navigation method) for detecting a position by integrating the speed and the traveling direction per unit interval using the position detection apparatus in the third embodiment for detecting the position and the traveling direction with the walker behavior detection apparatus. FIG. 11 shows a flowchart according to the fourth embodiment, FIG. 12 is an illustration of an example of a moving locus without compensation according to the second embodiment for comparison in the fourth embodiment, and FIG. 13 is an illustration for showing a result of the operation according to the fourth embodiment in the case of the same movement of the walker as that shown in FIG. 12.

Figure 12:
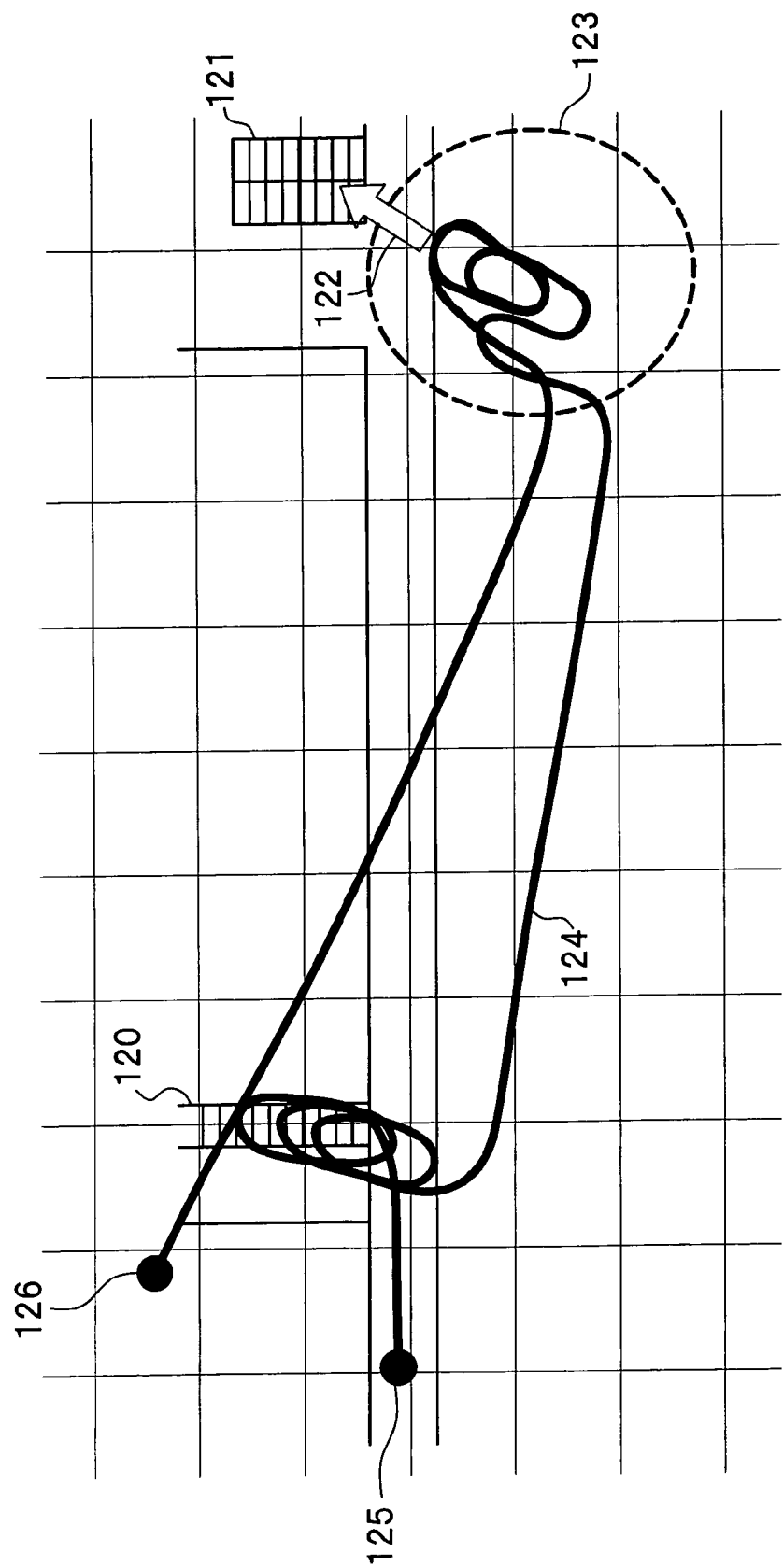
FIG. 12 is an illustration of an example of a moving locus without compensation according to the second embodiment for comparison in the fourth embodiment.
Figure 13:
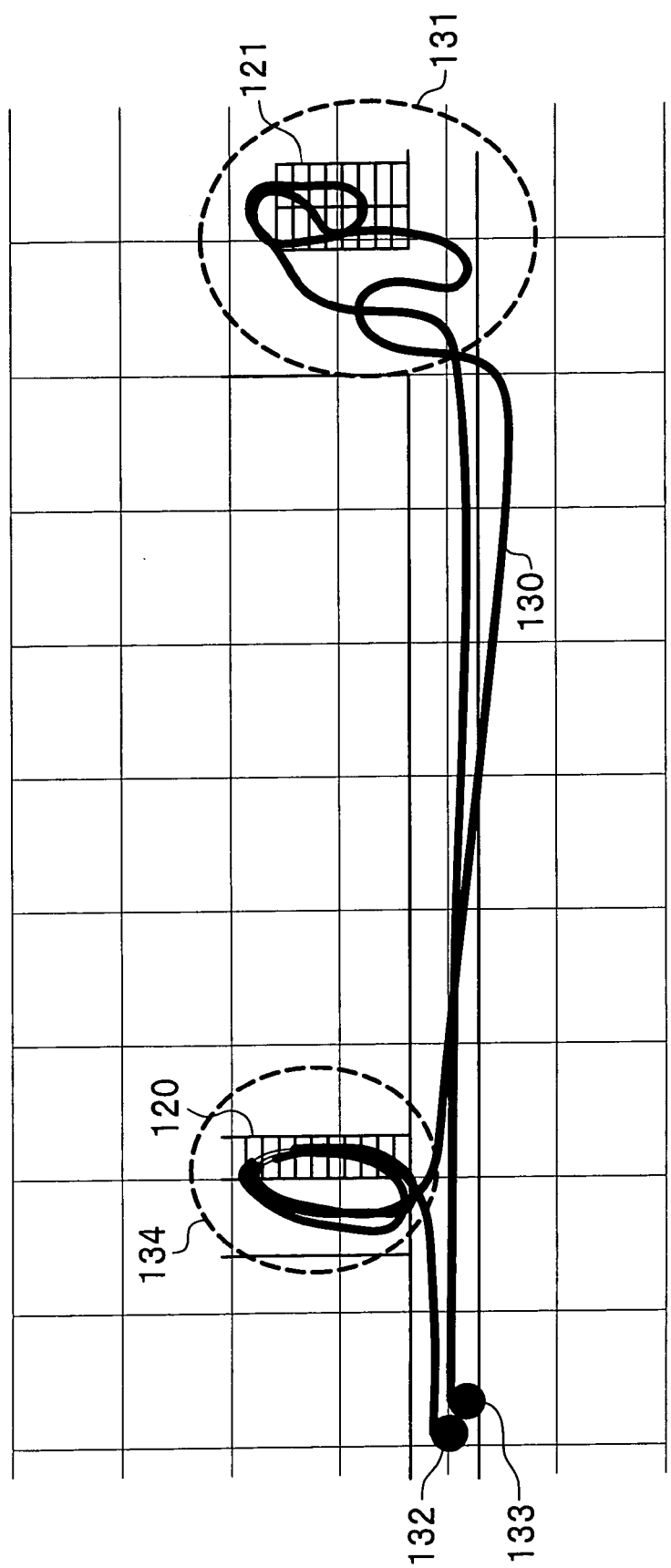
FIG. 13 is an illustration for showing a result of the operation according to the fourth embodiment in the case of the same movement of the walker as that shown in FIG. 12.

FIG. 12 shows an example of the moving locus obtained by the position detection apparatus shown in FIG. 7. Numeral 125 denotes a starting point. Numerals 120 and 121 denote staircases. An actual route in the example in FIG. 12 is that the walker starts at the starting point 125, ascends the staircase 120 across three floors, and moves on the three-floor-above floor toward the staircase 121, and descends the staircase 121 across three floors to return to the starting point 125. Numeral 124 denotes the moving locus detected by the position detection apparatus shown in FIG. 7. This shows an accurate moving locus from the starting point 125 to the staircase 120. However, after ascending the staircase 120, the moving locus 124 does not reach the position of the staircase 121 though the walker reaches a region 123 circled by a dotted line where the walker is supposed to be the staircase 121 because errors are accumulated in the direction due to drift of the direction detection sensor such as a gyro during ascending the staircase 120.

The embodiment provides a compensation apparatus for compensating the position for accuracy even in such a status. First, an initial position of the walker is set in a step 110 in FIG. 11. This may be done by entering positional coordinate values and a traveling direction after the walker confirms the position thereof with a map, an absolute position and a traveling direction, as input data, detected by a unit capable of detecting an absolute position such as the GPS unit if the walker is at an area where the unit can be used, or positional information detected by reading ID information after a tag and the like for transmitting ID information corresponding to the position is provided using an RFID and the like. A process of estimating the position and the traveling direction is made using the detected walking behavior and the geographical information in a step 111. This process can be done with, for example, the apparatus shown in FIG. 10. Next in a step 112, (1) a judgment is made whether estimation regarding the position and the traveling direction is possible, and (2) when the judgment is possible, the position and the traveling direction are calculated. If the estimation regarding the position and the traveling direction is possible, after the judging step 112, the current position and the traveling direction are set again using the estimated position and traveling direction in a step 113. The case that the estimation regarding the position and the direction are possible corresponds to the case that the corresponding place can be estimated through recognition between ascending and descending. For example, in the example in FIGS. 12 and 13, when the walker passes the staircases 120 and 121, this status can be detected and thus, the position of the staircase and the traveling direction are set again.

After that a walking speed per unit time interval is obtained and a traveling direction per the unit time interval (for example, the position detection apparatus shown in FIG. 7) are obtained in a step 114. Next, the moving locus is calculated by time-integration in a step 115 and a current position and a current traveling direction are outputted in a step 116. When it is judged that the estimation regarding the position and the traveling direction cannot be made in the step 112 (for example, in walking at a place other than the staircases); the processes in the step 114 and 115 are executed to output the current position and the current traveling direction in the step 116 without executing the setting process in the step 113. After this, processing returns to the step 111 to repeat these processes to continuously output the position and the traveling direction.

FIG. 13 shows a result of this operation according to the fourth embodiment in the case of the same movement of the walker as that shown in FIG. 12. The moving locus starting from the start point 132 is compensated so as to be identical with the position and an extending direction of the staircase 120, wherein cut portions halfway in the moving locus indicate places where the compensation is made. Further, when the walker advances to a region 131, the moving locus is compensated so as to be identical with the position and an extending direction of the staircase 121. Finally, the moving locus reaches the end 133. This is substantially the same position of the start point 132. Thus, this result shows that an accuracy in the position detection is made higher than that regarding the end point 126.

In the above-mentioned embodiment, the position compensation by the GPS unit is used for the initial position setting in the step 110. However, in the step 112, a judgment may be made whether an accuracy of the GPS unit is reliable and if the accuracy is reliable, in addition to the position compensation by the behavior detection, the compensation can be made with values from the GPS unit. Further, when both the position compensation by the behavior detection and the position detection by the GPS unit are judged to be possible, one of the position compensation by the behavior detection and the position detection by the GPS unit which has a higher accuracy is selected.

According to the fourth embodiment, this apparatus can be used as a compensating unit for the autonomous position detection apparatus in which an error is accumulated as time passes. For this operation, in FIG. 7, an inertial navigation system 74 including an acceleration sensor is added which compensates the position information and the traveling direction information from the inertial navigation system on the basis of the detected position and traveling direction.

Fifth Embodiment

Figure 14:
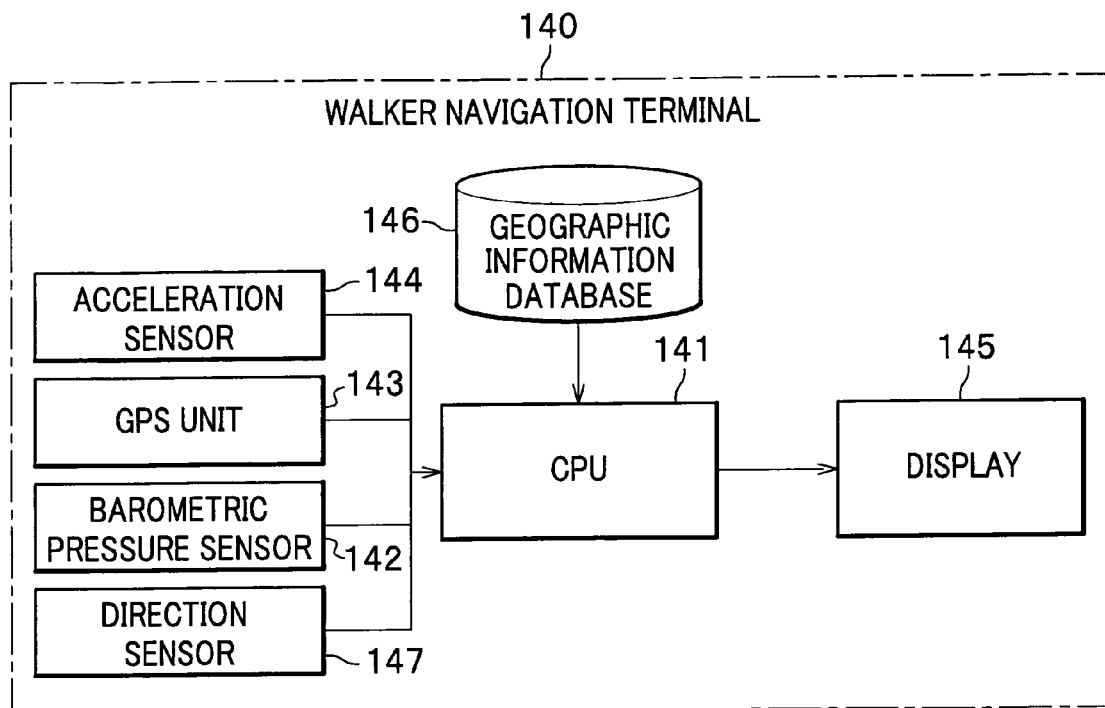
FIG. 14 is a block diagram of a walker navigation terminal using the walker behavior detection apparatus according to a fifth embodiment.

With reference to FIG. 14 will be described a walker navigation terminal according to a fifth embodiment using the walker behavior detection apparatus. In FIG. 14, numeral 144 denotes an acceleration sensor, numeral 142 denotes a barometric sensor, and numeral 147 denotes a direction sensor (a magnetic azimuth sensor or a gyro sensor). Numeral 143 denotes a GPS unit. Numeral 146 denotes a geographical information database, numeral 141 denotes a CPU as a processor, and numeral 145 denotes a display. These units are integrated as a walker navigation terminal 140 for a walker.

The acceleration sensor 144 corresponds to the behavior variation signal detecting unit 1 and the sensor 10 shown in FIG. 1, and the barometric pressure sensor 142 corresponds to the altitude detecting unit 3 in FIG. 1. The CPU 141 executes, on the basis of information from the acceleration sensor 144 and the barometric pressure sensor 142, the behavior detection of the walker described with reference to FIG. 1, the moving locus detection of the walker using an added direction sensor 147 described with reference to FIG. 7, and the position and direction detection using the behavior of the walker described using FIG. 10. Further in the GPS unit 143, in an open air where radio waves from GPS satellites can be received well, the position information obtained by the GPS unit 143 is used as the position of the walker navigation terminal without modification, or a value just before the receiving status becomes poor is used as setting information for the initial position in the step 110 in FIG. 11.

Numeral 146 denotes a geographical information database which is used for searching, from the detection result of the walking behavior, corresponding geographical information such as a position of a staircase and stores data for drawing the moving locus obtained by the moving locus detecting apparatus described with reference to FIG. 11 and geographic information of the circumference such as buildings and roads. A result obtained by the database 146 and the CPU 141 is drawn on a display unit 145. Among drawn information are the detection result of the walking behavior obtained with reference to FIG. 1, the burned calorie of the walker, the current moving locus of the walker, and the geographical information displayed over the moving locus obtained with reference to FIGS. 7, 10, and 11. This enables the walker to recognize where the walker is currently located by watching the display screen image 145.

In the embodiment, the method of detecting a current position of the walker and the moving locus is described. Route guidance on the basis of route search information which is generally performed in car navigation units may be performed on the basis of these pieces of information. Differences between the car navigation unit and the embodiment are as follows:

(1) At an area where the GPS can be used, the detection is the same as a car navigator. (2) When the GPS unit 143 cannot be used, in the embodiment the stride estimation is used though the car navigator detects a traveling distance using a vehicle speed pulse. (3) When a position detection error occurs, in the embodiment, the detected position is compensated with the geographical information of, for example, staircases, elevators, and escalators, corresponding to the walking behavior, though the car navigator compensates the detected position along roads (map-matching).

According to the fifth embodiment the walker navigator is provided.

Figure 15:
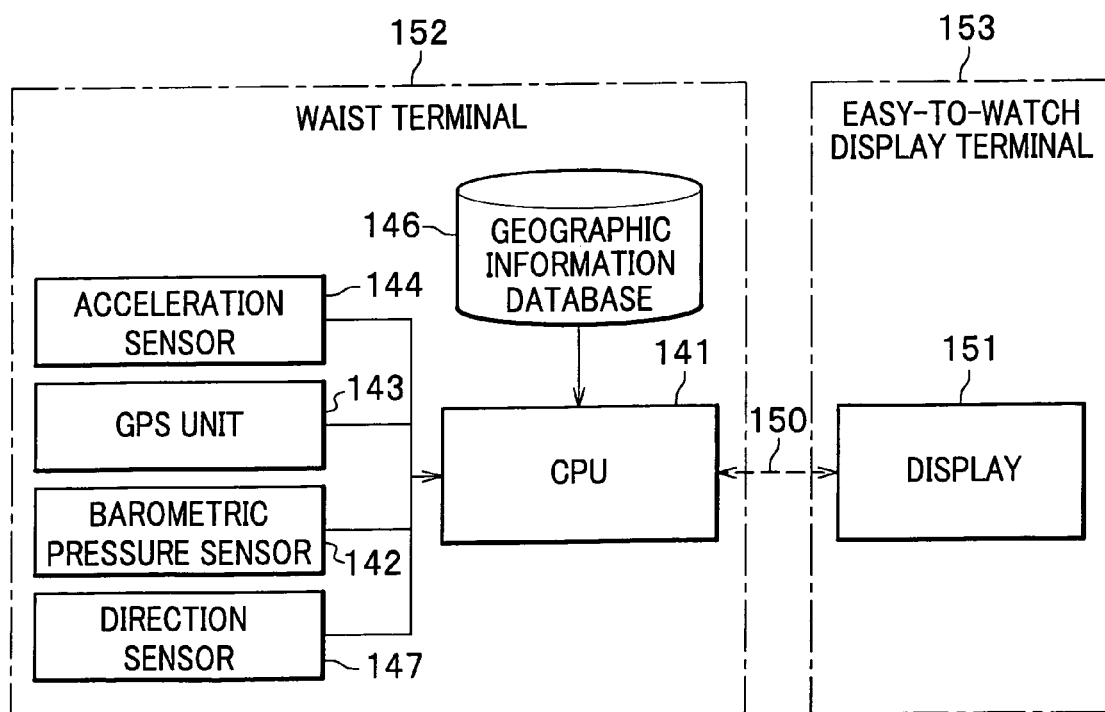
FIG. 15 is a block diagram of a walker navigation terminal using the walker behavior detection apparatus according to a modification in the fifth embodiment.

Next, a modification is shown in FIG. 15 in which a display terminal 151 is separated from a waist terminal 152. A difference from the walker navigation terminal shown in FIG. 14 is in that the display 151 is separated and the process is the same as that described with reference to FIG. 14.

To perform the behavior detection and the stride estimation of the walker, it is desirable to locate the acceleration sensor 144 and the direction sensor 147 at the waist of the walker which is the weight center of the walker. However, in the case of the example in FIG. 14, if the detection process is performed with the walker navigation terminal 140 being attached to the waist, the walker must watch the display screen to know the current place by detaching the walker navigation terminal 140 from the waist. This may cause an erroneous recognition or a position detection error in the detection result by the watching the display screen. Accordingly, in the example of FIG. 15, the walker navigation terminal is divided into a waist terminal 152, with a sensor part, attachable to the waist and an easy-to-watch display terminal 153 carried by a hand of the walker for providing a display screen on which image is displayed through transmitting and receiving information of screen image information and the like through communication line 150. The communication line 150 may be a wired one or a wireless one. This structure allows the walker navigation terminal to be divided into a display part of the easy-to-watch display terminal 153 and a sensor part of the waist terminal 152, in which the error recognition of the walking behavior and the position detection error are suppressed. More specifically, dividing the navigation terminal is made in order to locate the sensors for detecting walking behavior detection of the walker at the most appropriate place. In the structure shown in FIG. 15, the CPU 141 and the geographical information database 146 are arranged in the waist terminal 152. However, only the acceleration sensor 144 and the direction sensor 147 may be arranged in the waist terminal 152 attachable to the waist and other sensors and processing circuits may be arranged in the display terminal 153 for providing the screen image to the walker.

According to the embodiment, the sensors which may influence the detection accuracy of the walking behavior and the detection accuracy of the moving locus can be separately located at the place with a good condition.

Sixth Embodiment

Figure 16:
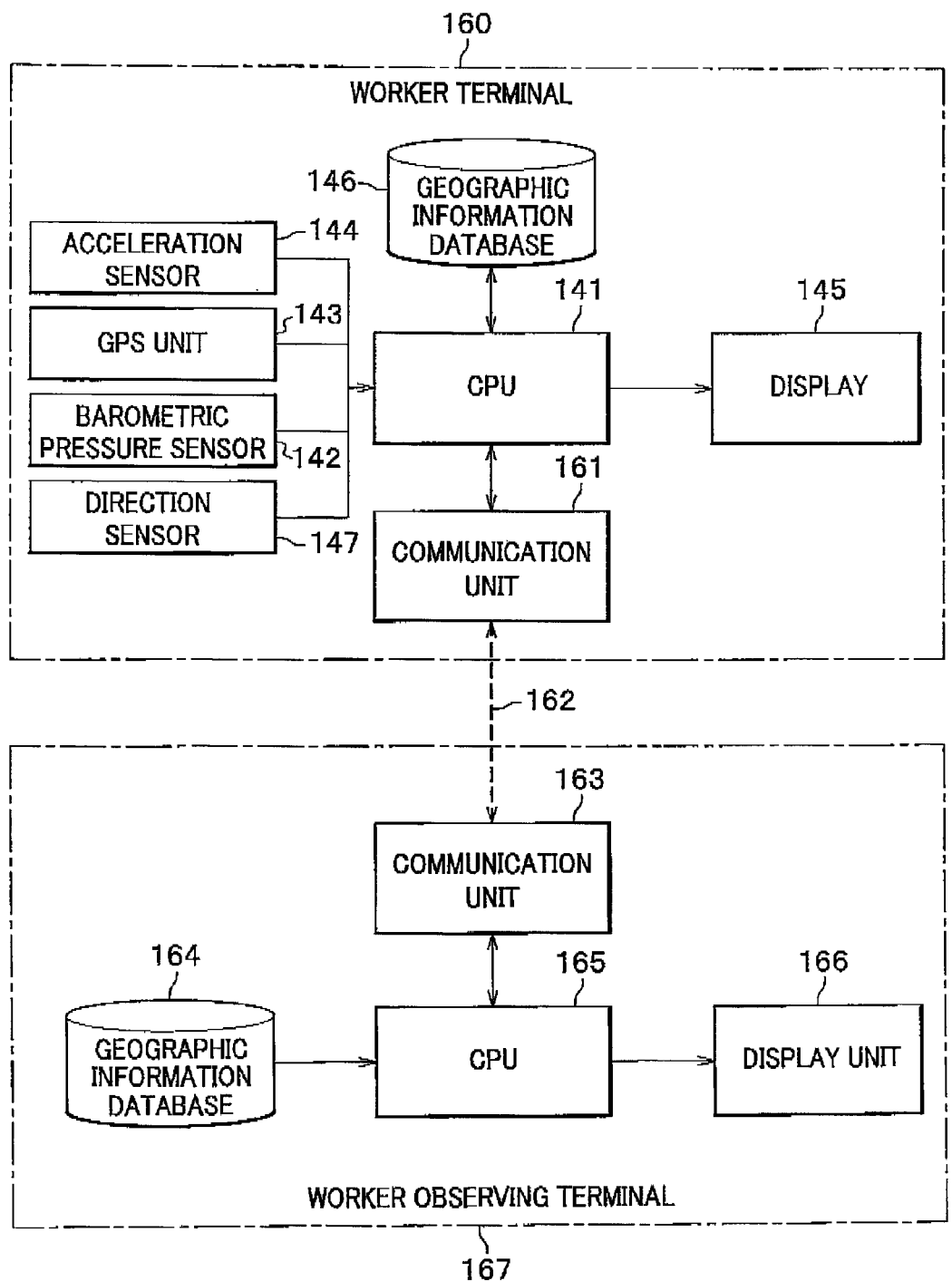
FIG. 16 is a block diagram of a worker status detection system using the walker behavior detection apparatus according to a sixth embodiment.

With reference to FIG. 16 will be described a sixth embodiment in which the present invention is applied to a worker status detection system. The system includes a worker terminal 160 attachable to a worker and a worker observing terminal 167 remote from the worker. The worker terminal 160 is provided with a communication unit 161 in addition to the structure described with reference to FIG. 14. Thus, the worker terminal 160 has a processing function described with reference to FIG. 14 to perform the detection of a behavior and a position of the worker and the detection of moving locus. These pieces of information can be watched by the worker with a display unit 145 similarly to the description made with reference to FIG. 14 and transmitted to the worker observing terminal 167 remotely located. Numeral 162 denotes a communication line such as a wireless communication. Numeral 163 denotes a communication unit, and numeral 164 denotes a geographical information database. Numeral 165 is a CPU as a processor, and numeral 166 is a display unit. The information, detected by the worker terminal 160, transmitted through the communication line 162 is received by the communication unit 163 to transmit it to a CPU 165 as a processor. The CPU 165 processes a drawing process of the transmitted information. For example, if a walker behavior detection result of the worker is transmitted, the result of the walker behaviors ("walking", "running", and "ascending" and the like) is converted into display image data to be transmitted to the display 166 for drawing. When the moving locus and position and traveling direction information are transmitted, it is possible to draw to indicate where the walker (worker) is located by overlapping the information on an image of the geographical information from the geographical database 164. Thus, the worker observing terminal 167 provides detection of a behavior and a position of a worker at a remote place. In FIG. 16, only one worker terminal is shown. However, a plurality of worker observing terminals may be wirelessly connected to the worker observing terminal 167 to display behavior information and position information of a plurality of workers. Further, the worker terminal 160 is a terminal in which the screen image and the sensors are integrated. However, the worker terminal 160 may be divided into a sensor part and the display part as described with reference to FIG. 15.

According to the embodiment, the position and the behavior of the worker can be detected at a remote place.

According to the above-mentioned embodiments, a combination of the walking behavior recognizing apparatus with assumption that it is used on the level and recognition by the barometric pressure variation provides recognition of the walker behavior accompanied by the vertical movement, and detection of burned calorie in accordance with the walking behavior.

Further, considering the barometric pressure variation only at the section where walking is accompanied by the vertical movement, provides the compensation for removing the influence of the see level pressure variation.

The stride can be estimated accurately though the walking behavior is accompanied by the vertical movement on, for example, the staircase. In addition, the moving locus can be estimated from the estimation of the stride.

The present invention provides the estimation of the place where the walker is by comparing the recognition result of the walking behavior with the geographical information, which provides a current position and the traveling direction of the walker.

The present invention is applicable to the compensating unit for the autonomous position detection apparatus to be used to compensating the position detected by the autonomous position detection apparatus in which an error is accumulated as time passes.

The present invention is applied to the walker navigator which is usable to observe the position and the behavior of the worker at a remote place.

As mentioned above, the present invention provides the walker behavior detecting apparatus capable of accurately recognizing the walking status though the walker in a walking status in which the walker moves vertically.

The invention claimed is:

1. A walking behavior detection apparatus for a walker comprising:
   first detecting means for detecting a horizontal walking behavior of a walker regarding a level;
   altitude variation detecting means for detecting altitude variation of the walker;
   estimating means for estimating a walking behavior of the walker on the basis of a combination of the horizontal walking behavior and the detected altitude variation, wherein said walking behavior comprises a plurality of distinct categories based on said combination;
   a database for storing geographical information corresponding to the detected behavior of the walker;
   a second detecting means for detecting a position and a traveling direction of the walker;
   change point detecting means for detecting a behavior change point of the walking behavior of the walker on the basis of the estimated walking behavior of the walker and a geographical change point being that geographical information stored in the database which corresponds to the estimated behavior of the walker; and
   compensating means for compensating the detected position of the walker and the detected traveling direction on the basis of the behavior change point and the geographical change point.

2. The walker behavior detection apparatus as claimed in claim 1, wherein the detecting means detects a behavior variation of the walker to generate a behavior variation signal and detects an amount of characteristic from the behavior variation signal using at least one of acceleration variation detection means for detecting an acceleration variation of the walker, means for detecting variation in electric field intensity, and a gyro sensor.

3. The walker behavior detection apparatus as claimed in claim 1, wherein the altitude variation detecting means comprises at least one of a barometric pressure sensor, a GPS unit, and an altitude detection means for detecting an altitude using a Radio Frequency Identification unit.

4. The walker behavior detection apparatus as claimed in claim 1, further comprising:
   a table showing a relation between a walking behavior and corresponding burned calorie; and
   obtaining means for obtaining and outputting a burned calorie of the walker with reference to the table and the estimated walking behavior.

5. The walker behavior detection apparatus as claimed in claim 1, further comprising:
   a navigation unit including a geographical database for storing geographical data and an outputting unit for providing navigation information to the walker on the basis of the estimated walking behavior and the geographical data.

6. The walker behavior detection apparatus as claimed in claim 1, further comprising:
   a worker terminal, including the recognizing means, carried by the walker; and
   a worker observing terminal, separated from the worker terminal, having communication unit for communicating with the worker terminal, for outputting the estimated walking behavior.

7. The walking behavior detection apparatus as claimed in claim 1, wherein the detecting means comprises:
   horizontal movement detecting means for detecting a horizontal movement of the walker;
   horizontal movement distinguishing means for distinguishing the horizontal movement with a vertical movement threshold to detect the horizontal walking behavior;
   vertical movement detecting means for detecting a vertical movement of the walker; and
   vertical movement distinguishing means for distinguishing vertical movement with a vertical movement threshold to detect the altitude variation of the walker.

8. The walking behavior detection apparatus as claimed in claim 1, further comprising vertical movement judging means for judging the altitude variation between presence and absence of the vertical movement, wherein the estimating means estimates the walking behavior on the basis of the combination of the horizontal walking behavior and the result of judging the altitude variation between presence and absence of the vertical movement.

9. The walker behavior detection apparatus as claimed in claim 8, further comprising:
   vertical movement extracting means for extracting at least a section on which the walker walks where the estimated walking behavior shows the presence of vertical movement and detecting an altitude variation in the extracted section; and
   integrating means for integrating the altitude variation of the walker only in the extracted section to determine an altitude variation of the walker.

10. The walker behavior detection apparatus as claimed in claim 8, further comprising:
    stride estimating means for, when the detecting means detects the walking behavior as walking on a level, estimating a stride of walking on the level; and
    compensating means for, when the detecting means detects the estimated walking behavior as walking with the presence of the vertical movement, compensating the estimated stride on the basis of the estimated walking behavior to obtain a moving speed and a traveling distance of the walker in accordance with the stride from the compensating means.

11. A walker behavior detection apparatus comprising:
    walker behavior detecting means for detecting a behavior of a walker;
    wherein said walking behavior comprises a plurality of distinct categories;
    a database for storing geographical information corresponding to the detected behavior of the walker;
    detecting means for detecting a position and a traveling direction of the walker;
    change point detecting means for detecting a behavior change point of the walking behavior of the walker on the basis of the estimated walking behavior of the walker and a geographical change point being that geographical information stored in the database which corresponds to the detected behavior change point as a position output and a traveling direction output from the geographic information in the database; and
    compensating means for compensating the detected position of the walker and the detected traveling direction on the basis of the behavior change point and the geographical change point which corresponds to the detected behavior change point with the position output and the traveling direction output.

12. The walker behavior detection apparatus as claimed in claim 11, further comprising:
   an inertial navigation system including an acceleration sensor for detecting a position and a traveling direction of the walker; and
   compensating means for compensating the position information and the traveling direction information from the inertial navigation system on the basis of the detected position and traveling direction.

13. A walking behavior detection apparatus for a walker comprising:
   first detecting means for detecting a horizontal walking behavior of a walker regarding a level;
   a database for storing geographical information corresponding to the detected behavior of the walker;
   altitude variation detecting means for detecting altitude variation of the walker;
   estimating means for estimating a walking behavior of the walker on the basis of a combination of the horizontal walking behavior and the detected altitude variation;
   second detecting means for detecting a position and a traveling direction the walker in which an error is accumulative;
   change point detecting means for detecting a behavior change point of the walking behavior of the walker and a geographical change point of geographical information corresponding to the detected behavior change point as a position output and a traveling direction output from the geographic information in the database; and
   compensating means for compensating the detected position and traveling direction of the walker on the basis of the geographical change point which corresponds to the detected behavior change point with the position output and the traveling direction output to suppress the error.

14. The walking behavior detection apparatus as claimed in claim 13, wherein the compensating means compensates the detected traveling direction of the walker on the basis of the behavior change point and the geographical change point to suppress the error.

* * * * *